United States Patent [19]

Margulies

[11] 4,333,457
[45] Jun. 8, 1982

[54] SELF-ASPIRATING SYRINGE WITH FRICTIONALLY ENGAGED LOCKING COLLET

[75] Inventor: Herman Margulies, South Orange, N.J.

[73] Assignee: Sterling Drug Inc., New York, N.Y.

[21] Appl. No.: 232,633

[22] Filed: Feb. 9, 1981

[51] Int. Cl.³ .............................................. A61M 5/22
[52] U.S. Cl. ............................ 128/218 R; 128/218 D
[58] Field of Search ........... 128/218 R, 218 D, 218 P, 128/218 PA, 218 F, 215, 276, 234, 224

[56] References Cited

U.S. PATENT DOCUMENTS

| | | | |
|---|---|---|---|
| 2,904,044 | 9/1959 | Jalar et al. | 128/218 DA |
| 3,115,135 | 12/1963 | Sarnoff | 128/218 DA |
| 3,224,445 | 12/1965 | Melott | 128/218 D |
| 3,295,525 | 1/1967 | Evers et al. | 128/272 |
| 3,340,872 | 9/1967 | Cox | 128/218 D |
| 3,433,223 | 3/1969 | Black | 128/218 D |
| 3,583,399 | 6/1971 | Ritsky | 30/40.1 |
| 3,739,780 | 6/1973 | Ogle | 128/220 |
| 3,797,487 | 3/1974 | Schmidt | 128/218 R |

FOREIGN PATENT DOCUMENTS 1508686 11/1967 France.

*Primary Examiner*—John D. Yasko
*Attorney, Agent, or Firm*—William G. Webb; B. Woodrow Wyatt

[57] ABSTRACT

A hypodermic syringe of the automatic or self-aspirating type for use in combination with disposable cartridge ampoules closed at the lower end by a diaphragm pierceable by a double-ended hypodermic needle and closed at the upper end by a slidable piston comprises a syringe holder adapted to generate aspirating conditions within the cartridge ampoule by the slight backward displacement of the slidable piston by means of a double plunger, one slidable within and biased against the other, the inner plunger being positively interengaged with the slidable piston of the cartridge ampoule, and axial movement of the outer plunger being restricted by frictional engagement with a collet in the end of the syringe holder.

10 Claims, 8 Drawing Figures

SELF-ASPIRATING SYRINGE WITH FRICTIONALLY ENGAGED LOCKING COLLET

BACKGROUND OF THE INVENTION

In medical practice, hypodermic injections are sometimes administered subcutaneously, while others must be given intravenously, depending upon the particular medication to be administered. In either case, it is essential that the practitioner know with certainty, prior to injection of the medication whether the hypodermic needle tip is located in a major blood vessel, such as a vein, or in subcutaneous tissue. Use of an aspirating syringe in which a negative pressure can be generated in the syringe affords a means of making such determination. Thus the appearance of blood in the syringe upon generation of the negative pressure would indicate location of the needle tip in a major blood vessel, while the lack of appearance of blood would indicate location of the tip in subcutaneous tissue. Depending upon the type of injection intended, the injection can then either proceed directly, or if appropriate the tip can be withdrawn and relocated.

Aspirating syringes useful for the above stated purpose are generally of two types, that is either manually or automatically actuated. It is conventional in both manual as well as automatic aspirating syringes to use cartridge ampoules of the disposable, pre-loaded type, the lower end of which is closed by a flexible rubber diaphragm, which is pierceable by one end of a double-ended needle and secured to the ampoule by a crimped-on overcap, the upper end being closed by a piston slidable within the bore of the cartridge ampoule.

Syringes of the automatic aspirating type are often referred to as self-aspirating syringes. The syringes provided by the present invention are of the latter type and are used in conjunction with disposable cartridge ampoules of the type described above.

THE PRIOR ART

Aspiration in syringes of the manual type used with cartridge ampoules is usually effected by slightly withdrawing the syringe plunger rod after it has been connected to the slidable ampoule piston. Connection between the plunger rod and the slidable piston can be effected by a variety of means, such as by a screw-threaded engagement as in Schmidt, U.S. Pat. No. 3,797,487; by an interlocking jaw/coupling button as in Sarnoff, U.S. Pat. No. 3,115,135; or by a barb or "harpoon" on the syringe plunger which pierces and engages the rubber piston as in Jalar et al., U.S. Pat. No. 2,904,044 or Melott, U.S. Pat. No. 3,224,445. Alternatively, the body of the ampoule itself is withdrawn after locking a slidable ampoule piston to a central hollow post in the syringe body, for example by a screw-threaded engagement, as in Ogle, U.S. Pat. No. 3,739,780. Such manually actuatable aspirating syringes, however, have the disadvantage that their proper use depends in very large measure on the degree of skill of the person administering the injection.

Aspiration in syringes of the automatic or self-aspirating type is effected by first inducing a positive pressure in a medicament-containing portion of the syringe, for example in a disposable cartridge ampoule. On release of the force inducing the positive pressure, a corresponding negative pressure in the syringe is generated thus giving rise to the aspirating effect. In Ritsky, U.S. Pat. No. 3,583,399, induction of the positive pressure is achieved by the inward flexing of a rubber diaphragm, which closes the lower end of a medicament-containing ampoule and which is pierceable by the inner end of a double-ended needle, such flexing resulting from impingement of the lower end of the ampoule against a fixed stud surrounding the inner end of the double-ended needle when the ampoule is pressed downwards. Release of the pressure against the ampoule causes return of the diaphragm to its original planar configuration and consequent generation of a slight negative pressure in the ampoule. Self-aspirating syringes of the type described by Ritsky however have the disadvantage that the self-aspirating effect depends greatly on the elasticity of the rubber diaphragm, and the elasticity in turn depends on a number of other variables such as the type, quality and thickness of the rubber and the size of the opening in the end of the ampoule over which the rubber diaphragm is stretched. Thus, syringes equipped with the stud-actuated self-aspirating feature require the use of carefully standardized ampoules.

In Evers et al., U.S. Pat. No. 3,295,525 and Cox, U.S. Pat. No. 3,340,872, induction of the positive pressure in the medicament-containing ampoule is achieved by the action of a flexible portion of the slidable rubber piston which closes the upper end of the ampoule. In these devices, downward pressure on the syringe plunger causes inward distention of the flexible portion of the rubber piston thus producing the desired positive pressure in the ampoule. Release of pressure against the plunger results in return of the flexible portion to its undistended condition and consequent generation of a slight negative pressure in the ampoule. Self-aspirating syringes of the type described by Evers et al. and Cox suffer from the disadvantage that the rubber pistons, with the flexible portions as an integral part thereof, require special molding and are thus more expensive than conventional rubber pistons.

A rather elaborate method of achieving self-aspiration in a hypodermic syringe unit is that shown by Black U.S. Pat. No. 3,433,223 which describes a gas powered injection system in which self-aspiration is generated by holding the piston of a cartridge ampoule stationary while the ampoule is moved forward, thus in effect producing a backward motion of the piston.

BRIEF SUMMARY OF THE INVENTION

Ideally a self-aspirating hypodermic syringe employing disposable cartridge ampoules should be relatively simple in construction so as to minimize the cost of production; should be relatively simple to operate; should be capable of manipulation with one hand; should be adaptable to multiple self-aspirating actions with each ampoule; should be capable of expelling trapped air from the ampoule prior to insertion of the needle into the injection site and prior to initiation of the self-aspirating action without either precluding self-aspirating action at a later time in the operation sequence of the syringe or otherwise rendering it inoperative; and should be so-constructed that the self-aspirating hypodermic syringe, either in whole or in part, can be marketed either as single-use disposable (i.e. plastic) units or as reusable units marketed as a self-aspirating hypodermic syringe unit for use in combination with the cartridge ampoules.

The self-aspirating syringes provided by the present invention mimic, automatically, the slight rearward piston displacement withdrawal action of manually operable syringes, thus generating the slight negative pressure in the cartridge ampoule essential for aspiration. The syringes of the present invention therefore obviate the disadvantages inherent in prior art syringes of the manual type, since the aspirating action is generated automatically which requires no special skill on the part of the practitioner. They also obviate the disadvantages of syringes of the automatic (i.e. self-aspirating) type, because aspirating action is achieved independently of the elasticity of the rubber diaphragm of the cartridge ampoule, and they utilize cartridge ampoules with standard rubber pistons. The syringes provided by the invention moreover achieve each of the above-indicated objectives of an ideal self-aspirating syringe.

More specifically the present invention is directed to a hypodermic syringe holder having holding means within the head thereof adapted to securely hold within the barrel thereof a medicament containing cartridge ampoule, the syringe holder being provided with a pair of plungers, one slidable within the other, said plungers being biased one against the other, the inner plunger being adapted for positive interengagement with the slidable piston of the cartridge ampoule, and free axial movement of the outer plunger being restrictable by means of frictional engagement thereof with a collet located in the head of the syringe holder, whereby upon alternate exertion of downward pressure upon the inner plunger and release thereof when the outer plunger is so restricted, the bias of one plunger against the other produces slight withdrawal of the slidable piston in the cartridge ampoule thereby generating aspirating conditions in the latter.

BRIEF DESCRIPTION OF THE DRAWINGS

The invention is described hereinbelow with reference to the accompanying drawings wherein.

DETAILED DESCRIPTION OF THE INVENTION

The invention will now be described in detail with reference to the foregoing figures where like numerals are used to designate like parts.

In the foregoing discussion and elsewhere in the specification and appended claims, the terms "lower" and "downward" are intended to make reference to the needle end of the hypodermic syringe and associated parts described herein, and conversely the terms "upper" and "upward" are intended to make reference to the head end thereof.

Figure 6:
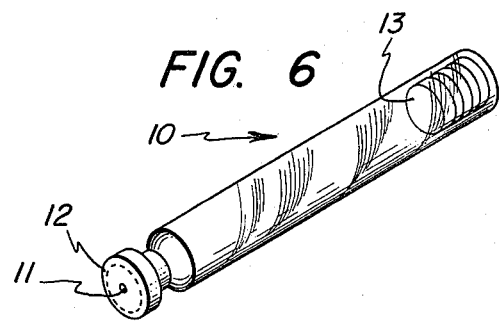
FIG. 6 is a perspective view of a cartridge ampoule used with the self-aspirating syringes of the invention.

FIG. 6 illustrates a cartridge ampoule, generally indicated by reference numeral 10, of a well known type which consists of a cylindrical container, usually glass or clear plastic, having a necked-down end and sealed at the necked-down end with a rubber diaphragm 11 which is secured to the ampoule by a crimped on metal collar 12. The other end of the ampoule is closed by a piston 13 which is slidable within the bore of the ampoule.

Figure 1A:
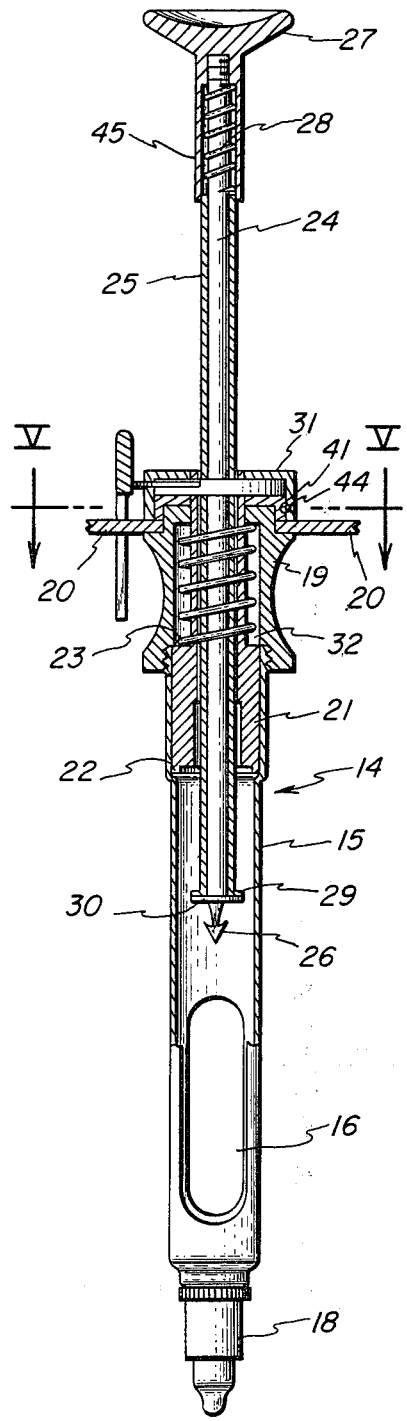
FIG. 1A is a view in partial longitudinal section of one embodiment of a self-aspirating syringe of the invention.

The self-aspirating concept of the present invention is used in conjunction with syringe holders of the side-loading type. One such embodiment, generally indicated by the reference numeral 14, is illustrated in FIG. 1A. The syringe there depicted is composed of a hollow tubular body or barrel 15 having an elongated window 16 therein for insertion of a cartridge ampoule 10, only the lower end of window 16 being depicted in the partial section views of FIGS. 1A and 1B. The syringe holder is fitted at its lower end with a needle hub unit 18, which is either detachably or integrally fitted with a hypodermic needle (not shown), the needle hub unit itself being detachably fitted to the syringe holder, for example by means of a screw-threaded mounting. The needle is of the double ended type so that when a cartridge ampoule 10 is in place within the syringe barrel 15, the inner end of the needle pierces the rubber diaphragm 11 so that the needle is in communication with the contents of the ampoule. The barrel 15 extends from a head unit 19 to which is attached a pair of finger grips 20.

In the practice of the present invention, it is necessary that the ampoule 10 be essentially immobilized within the barrel 15 of the syringe holder, and accordingly for this purpose the head 19 is equipped with a locking sleeve 21 of generally cylindrical configuration, the shoulder 22 of which is biased downwards against the rim of the cartridge ampoule by compression spring 23. Slidably mounted in the bore of the locking sleeve is a double plunger which comprises an inner plunger rod 24 which itself is slidable within the bore of a sleeve or outer plunger 25. The inner plunger rod is fitted at its lower end with any conventional means for making positive interengagement with the piston 13 in the cartridge ampoule 10. For purposes of illustration this interengagement means is depicted herein as a barbed point or "harpoon" 26 which is well known in the art for the stated purpose. However, it is to be understood that any conventional means of making such interengagement, for example by the various means discussed in the PRIOR ART section above, will serve the purpose as well. The upper end of the inner plunger is fitted with a thumb plate 27 with a skirt 45 depending therefrom, and the inner plunger and outer plunger or sleeve are biased, one against the other, by a coil spring 28.

The lower end of the outer plunger or sleeve is fitted with an annular rim 29 which serves to prevent removal of the inner/outer plunger assembly from within the bore of the locking sleeve 21. The lower end of the inner plunger or rod is also fitted with an annular rim 30 which serves to prevent removal of the inner plunger from within the bore of the outer plunger or sleeve. The thumb plate and skirt unit are threadably engaged with the upper end of the inner plunger. The threaded interengagement of the thumb plate and skirt unit with the plunger provides a means for assembling the inner/outer plunger unit within the head of the syringe. This assembly is accomplished by first removing the thumb plate/skirt/coil spring units 27/45/28 from the outer plunger, passing the inner and outer plungers one within the other, through window 16 and upward through the bore of locking sleeve 21 and reassembling the coil spring and thumb plate/skirt units to the inner plunger.

The locking sleeve 21, at its widest diameter, is slidable within the bore of the syringe head 19, and at its upper end has a section of diminished diameter which is slidable through the end opening of the syringe head and the opening through a clutch assembly 31 to be described hereinbelow. The upper end of the locking sleeve passes through a cavity 32 in the head of the syringe which is of sufficient diameter to accommodate a compression spring 23, which, as pointed out above, serves to bias the shoulder 22 of the locking sleeve 21 downwards against the rim of the ampoule 10.

Figure 2A:
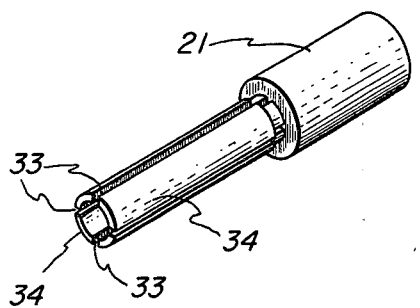
FIG. 2A is a perspective view of a collet/locking sleeve used with the embodiment of FIG. 1A.

The locking sleeve 21 as described above is best seen by reference to FIG. 2A. The upper end of the locking sleeve 21 having the smaller diameter is provided with slots 33 which define an equal number of flexible fingers 34.

Figure 3A:
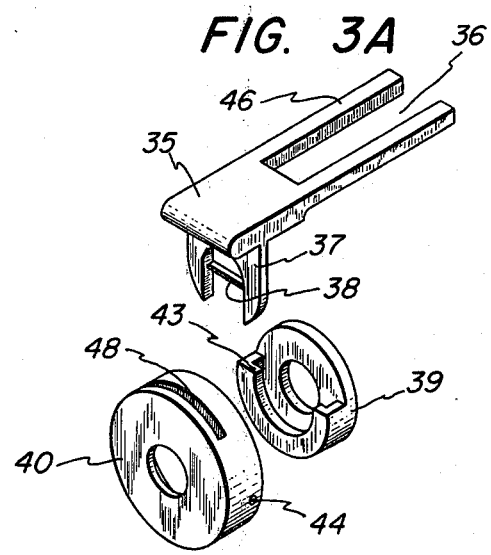
FIG. 3A is an exploded perspective view of a clutch assembly used with the embodiment of FIG. 1A.

The clutch assemby 31 mentioned above is fitted to the head 19 of the syringe holder and, with reference to FIG. 3A, consists of a generally U-shaped pressure plate 35, the extensions 46 of which provide finger bearing surfaces which define the sides of a notched section 36. Attached to the pressure plate 35, generally normal to the plane thereof, is a flat yoke 37. The yoke is fitted with a leaf spring 38 across the throat of the yoke. The yoke is slidably mounted in face plate 39 by means of flanges 43, and the yoke/face plate assembly is covered by a collar 40.

Figure 5:
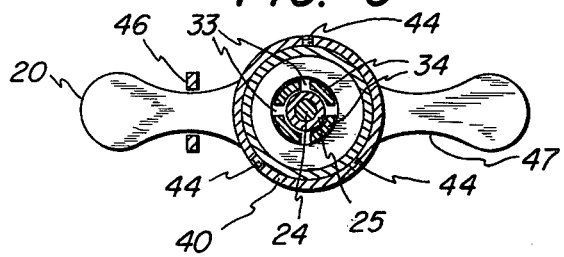
FIG. 5 is a view in transverse section on line V—V of FIG. 1.

The method of securing the clutch assembly to the syringe head is best seen by reference to FIGS. 1A, 3A and 5. Thus the face plate 39 is covered by collar 40 and yoke 37 is engaged with the assembly by inserting the yoke through yoke plate opening 48 in collar 40, the legs of the yoke thus being slidably engaged under flanges 43 in face plate 39. The resulting assembly is then placed over the upper end of locking sleeve 21, while engaging the two extensions 46 one on either side of a constricted section 47 of one of the finger grips 20. (See FIG. 5). The wider terminal portion of the finger grip 20 serves to retain the yoke and associated finger plate in engagement with face plate 39. The entire assembly is then secured to the syringe head by means of set screws 44 which bear against surface 41 of the head. (See FIG. 1A).

In an alternative assembly of clutch 31 (not depicted), the face plate 39 is eliminated, and the flanged section 43 is incorporated within the base of collar 40, the flanges of course opening to the bottom of collar 40 rather than to the top as is necessary when face plate 39 is used. In this alternative assembly, the yoke 37, without leaf spring 38 fitted thereto, is inserted through yoke plate opening 48 in the side of collar 40. The height of leaf spring 38 is chosen so as to be greater than either the thickness of yoke 37 or the height of yoke plate opening 48. Thus when the leaf spring is inserted in the throat of the yoke opening, it serves to retain the yoke within collar 40. The assembly is then attached to the syringe head in the same manner described above.

In use, the embodiment of FIG. 1A is first loaded with a cartridge ampoule 10 by withdrawing the plunger/locking sleeve against the bias of compression spring 23, inserting the ampoule through window 16, and releasing the plunger/locking sleeve. Engagement between the inner plunger rod 24 and piston 13 is made, and in syringes having a detachable needle and needle hub unit, such unit is then attached. After air is expelled from the cartridge by downward pressure on the thumb plate 27, the needle is inserted into the injection site. When the practitioner wishes to aspirate in order to determine whether the needle tip has pierced a vein, finger pressure against extensions 46 of finger plate 35 is exerted which causes the leaf spring 38 in the yoke 37 to impinge upon at least one of the flexible fingers 34 of the locking sleeve 21 forcing the fingers to make frictional contact with the outer surface of outer plunger or sleeve 25. With the frictional resistance to axial movement of the outer plunger thus produced, further downward pressure on thumb plate 27 will enable the inner plunger or rod 24 to advance beyond the outer plunger 25, and these elements will assume the relative positions with respect to one another indicated in FIG. 4. When pressure on the thumb plate 27 is released, the inner plunger or rod will be withdrawn by the force generated by coil spring 28, and the inner and outer plungers will once again assume the relative positions with respect to one another indicated in FIG. 1A. As the inner plunger is withdrawn the rubber piston 13 to which it is firmly engaged via interengagement means 26 is likewise withdrawn slightly thus generating slight negative pressure in the ampoule which is necessary for aspirating action. Thus it is seen that the locking sleeve 21 serves a dual purpose as a locking sleeve to immobilize the cartridge ampoule in the syringe barrel and as a collet to create frictional resistance against axial movement of the outer plunger 25.

Although this embodiment has been described by reference to the leaf spring 38 within yoke 37, it will be appreciated that alternative means of making engagement between the yoke and fingers 34 can be used, for example by restricting the throat portion of the yoke opening.

Figure 1B:
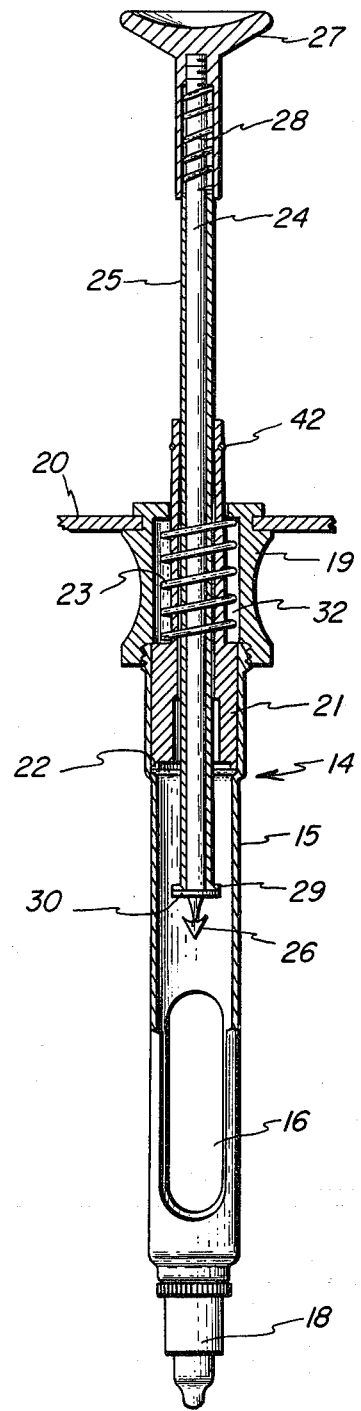
FIG. 1B is a view in partial longitudinal section of a second embodiment of a self-aspirating syringe of the invention.
Figure 2B:
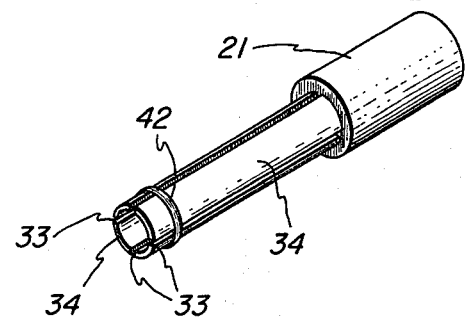
FIG. 2B is a perspective view of a collet/locking sleeve used with the embodiment of FIG. 1B.
Figure 4:
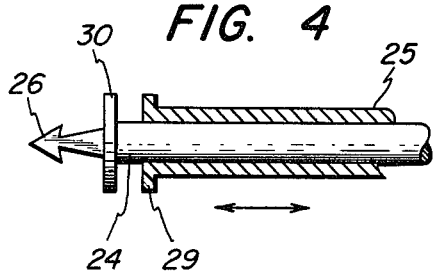
FIG. 4 is an elevational view of the inner end of a double plunger used with the embodiments of FIG. 1A and FIG. 1B illustrating the plunger mechanism in an aspirating mode.

A further embodiment of the invention, which employs the same principle of creating frictional resistance to axial movement of the outer plunger of a double plunger unit, is illustrated in FIG. 1B. In this embodiment the flexible fingers 34 forming the collet are grooved near the free ends thereof, and a choke ring 42, shown in FIG. 2B, such as a strong wire is seized around the fingers in the groove. The tension of the ring is so adjusted that there will be a constant frictional resistance to downward movement of the outer plunger when pressure is applied to the thumb plate. Thus in use the inner plunger will always be advanced beyond the outer plunger, while coil spring 28 will be under continuous compression. Thus during the downstroke of the thumb plate, the inner and outer plunger elements will always have the relative positions with respect to one another as depicted in FIG. 4. As with the embodiment of FIG. 1A, when downward pressure on the thumb plate is released, the inner plunger is withdrawn under the force generated by coil spring 28 thereby generating aspirating conditions in the ampoule. Therefore the syringe depicted in FIG. 1B has a constant capability for generation of aspiration at any point during the downstroke of the plunger mechanism without the need to make further manipulations in the instrument as in the embodiment in FIG. 1A.

It will be appreciated from the foregoing description that the self-aspirating syringes of the instant invention possess all the attributes of an ideal aspirating syringe as enumerated above. That is the syringes are relatively simple in construction, thus minimizing the cost of production; they are relatively simple to operate; they are capable of manipulation with one hand; they are capable of multiple self-aspirating actions with each cartridge ampoule; and they are capable of expelling air trapped within the ampoule either prior to initiation of the self-aspirating action or at any time during the sequence of actions necessary for injection of the ampoule contents without, on the one hand, precluding self-aspirating action at any point in the sequence or, on the other, rendering the self-aspirating action inoperative.

Moreover the syringes of the invention can be constructed either in whole or in part from metal, to provide reusable units, or from plastic, to provide disposable units.

It will also be understood that, although the preferred embodiments of the invention have been described above in order to better illustrate the same, alternative structural features can be substituted for elements described herein without either departing from the spirit of the invention or in any way adversely affecting the operability of the same. For example, as mentioned above, alternative conventional means of achieving interengagement between the inner plunger and the slidable ampoule piston can be used. Furthermore a thumb ring, conventionally used in manually operating aspirating syringes, although not essential in the operation of the present automatic self-aspirating system, can nonetheless be used in place of a thumb plate.

Having thus described the invention and the advantages thereof, it is considered that the invention is to be broadly construed and limited only by the character of the following claims.

I claim:

1. A self-aspirating hypodermic syringe of the type used in combination with a cartridge ampoule which is sealed at its upper end by a slidable piston and at its lower end by a pierceable membrane, and which contains an injectable fluid therein, which comprises a syringe holder having:
   (A) a head;
   (B) a barrel attached thereto for receiving said cartridge ampoule and provided at its lower end with a double ended needle for communication with the cartridge ampoule contents; and
   (C) a generally cylindrical holding means within said head,
said holding means being adapted:
   (1) to securely hold said cartridge ampoule within said barrel;
   (2) to receive within the bore thereof a double plunger mechanism comprising an inner plunger slidable within the bore of, and biased against, an outer plunger, said inner plunger having interengagement means for making positive interengagement with the slidable piston closing the upper end of said cartridge ampoule; and
   (3) to generate frictional resistance to axial movement of said outer plunger,
whereby upon alternate exertion of downward pressure upon said inner plunger and release thereof when said frictional resistance is generated, the bias of said inner plunger against said outer plunger creates aspirating conditions in said ampoule.

2. The self-aspirating syringe according to claim 1 wherein said holding means is a spring biased locking sleeve, the upper end of which is slotted about its periphery to form flexible collet fingers adapted to engage said outer plunger to thereby generate frictional resistance to axial movement thereof.

3. A self-aspirating syringe according to claim 2 wherein the bias between the inner and outer plungers is generated by a coil spring.

4. A self-aspirating syringe according to claim 3 wherein the head of said syringe is provided with a clutch assembly for generation of frictional resistance to axial movement of said outer plunger.

5. A self-aspirating syringe according to claim 3 wherein said generally cylindrical holding means comprises a collet adapted for continuous engagement of said flexible collet fingers with said outer plunger.

6. A self-aspirating syringe according to claim 4 wherein said clutch contains a finger pressure plate generally normal to a yoke, said yoke having means for frictional engagement with said outer plunger.

7. A self-aspirating syringe according to claim 5 wherein said collet fingers are provided with a choke.

8. A self-aspirating hypodermic syringe according to claim 7 wherein said choke comprises a wire secured in a groove around the ends of the collet fingers.

9. A self-aspirating hypodermic syringe according to claim 6 having a threadably detachable needle and needle hub unit.

10. A self-aspirating hypodermic syringe according to claim 8 having a threadably detachable needle and needle hub unit.

* * * * *